United States Patent
Hu

(10) Patent No.: US 7,500,185 B2
(45) Date of Patent: Mar. 3, 2009

(54) FRAMEWORK OF VALIDATING DICOM STRUCTURED REPORTING DOCUMENTS USING XSLT TECHNOLOGY

(75) Inventor: Jingkun Hu, Pleasanton, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 469 days.

(21) Appl. No.: 11/117,111

(22) Filed: Apr. 28, 2005

(65) Prior Publication Data

US 2005/0246629 A1 Nov. 3, 2005

Related U.S. Application Data

(60) Provisional application No. 60/614,733, filed on Jan. 3, 2005, provisional application No. 60/566,463, filed on Apr. 29, 2004.

(51) Int. Cl.
*G06F 15/00* (2006.01)
*G06F 17/00* (2006.01)

(52) U.S. Cl. .................. 715/235; 715/236; 715/249; 382/128; 382/131; 382/132; 707/102; 707/204

(58) Field of Classification Search ................ 715/513, 715/523, 530, 512, 516; 382/132, 131, 128; 707/102, 204

See application file for complete search history.

(56) References Cited

U.S. PATENT DOCUMENTS

| | | | | |
|---|---|---|---|---|
| 5,708,828 | A * | 1/1998 | Coleman | 715/523 |
| 6,151,608 | A * | 11/2000 | Abrams | 707/204 |
| 2002/0143727 | A1* | 10/2002 | Hu et al. | 707/1 |
| 2002/0143824 | A1* | 10/2002 | Lee et al. | 707/523 |
| 2003/0055806 | A1* | 3/2003 | Wong et al. | 707/1 |
| 2004/0252871 | A1* | 12/2004 | Tecotzky et al. | 382/128 |
| 2005/0244041 | A1* | 11/2005 | Tecotzky et al. | 382/128 |
| 2006/0282447 | A1* | 12/2006 | Hollebeek | 707/101 |

OTHER PUBLICATIONS

Lee, K. P., et al., XML Schema Representation of DICOM Structured Reporting, Mar.-Apr. 2003, Journal of the American Medical Informatics Association, 10:213-223.*

* cited by examiner

*Primary Examiner*—Doug Hutton
*Assistant Examiner*—Nathan Hillery

(57) ABSTRACT

Methods, frameworks and systems for validating DICOM (Digital Imaging and Communications in Medicine) SR (Structured Reporting) XML (Extensible Markup Language) documents against DICOM SR templates, using XSLT (Extensible Stylesheet Language Transformations) technology alone or as a complement to XML Schema, are disclosed. A framework of generating XSLT stylesheets from XML representation of DICOM SR templates is developed. Also a mechanism and method of automatic generating XSLT stylesheets for validating SR document contents are provided. In addition, a mechanism and method of flexibly adapting in different DICOM SR XML formats is provided.

4 Claims, 10 Drawing Sheets

FRAMEWORK OF VALIDATING DICOM STRUCTURED REPORTING DOCUMENTS USING XSLT TECHNOLOGY

CROSS REFERENCE TO RELATED APPLICATION

This is a continuation of prior applications Ser. Nos. 60/566,463, filed Apr. 29, 2004 and 60/614,733, filed Jan. 3, 2005.

FIELD OF USE

This invention relates to the validation of medical reports, especially to methods, frameworks and systems for validating medical type reports using DICOM (Digital Imaging and Communications in Medicine) Structured Reporting formats.

BACKGROUND AND PRIOR ART

The Digital Imaging and Communications in Medicine (DICOM) Structured Reporting (SR) standard, and the SR Documentation Model upon which it is based, improves the expressiveness, precision, and comparability of documentation of diagnostic images and waveforms. DICOM SR supports the interchange of expressive compound reports in which the critical features shown by images and waveforms can be denoted unambiguously by the observer, indexed, and retrieved selectively by subsequent reviewers. Findings may be expressed by the observer as text, codes, and numeric measurements, or via location coordinates of specific regions of interest within images or waveforms, or references to comparison images, sound, waveforms, curves, and previous report information. The observational and historical findings recorded by the observer may include any evidence referenced as part of an interpretation procedure.

Thus, DICOM SR supports not only the reporting of diagnostic observations, but the capability to document fully the evidence that evoked the observations. This capability provides significant new opportunities for large-scale collection of structured data for clinical research, training, and outcomes assessment as a routine by-product of diagnostic image and waveform interpretation, and facilitates the pooling of structured data for multi-center clinical trials and evaluations. See "Clinical Rationale for the SR Documentation Model and the DICOM Structured Reporting (SR) Standard", Abstract, W. Dean Bidgood, Jr., © 1999.

The DICOM SR is based on a relational data technology, and has been standardized by the National Electrical Manufacturers Association (NEMA). DICOM SR supports not only the reporting of diagnostic observations, but can document fully the evidence that evoked the observations. This move toward structured, coded reports presents new care-improvement opportunities beyond mere storage and distribution. Coding medical information for selective retrieval allows computers to assist in processing the increasingly large amounts of clinical data collected during normal operation of a healthcare enterprise. When judiciously combined with knowledge-based information processing we can significantly enhance clinical decision-making.

As with any structured data in healthcare, benefits exist in outcome analysis and point-of-care applications. SR in its most general form is very flexible and the same content can be expressed in different forms and structures, hampering interoperability. Templates are a means to put additional constraints on an SR document to promote common formats for specific reporting applications. DICOM part 16 DCMR (DICOM Content Mapping Resource) [2] defines general SR templates and Mammography CAD SR IOD templates. Additional templates for other specialties are being developed such as:

Supplement 26: Ultrasound OB-GYN Procedure Reports
Supplement 66: Catheterization Lab SR SOP Classes
Supplement 71: Vascular Procedure Reports
Supplement 72: Echocardiography Procedure Reports Although the DICOM SR standard provides for a consistent reporting and recording scheme, the use of the information contained in a DICOM SR is limited to DICOM compliant applications that can process this information using the DICOM specific format. Application developers must be DICOM literate, and a methodology for deploying applications that interoperate with other applications outside the DICOM domain has not yet been developed.

In the computer industry, progress has been made in the use of standardized languages and methodologies that facilitate the use of information from a variety of sources by a variety of applications. A standard language that is widely used for processing content material is the World Wide Web Consortium (W3C) Extensible Markup Language (XML), which is derived from the Standard Generalized Markup Language (SGML), and is designed to describe data and its structure so that it can be easily transferred over a network and consistently processed by the receiver. Because XML is used to describe information as well as structure, it is particularly well suited as a data description language.

One of the particular strengths of XML is that it allows entire industries, academic disciplines, and professional organizations to develop sets of Document Type Definitions (DTDs) and Schemas that can serve to standardize the representation of information within those disciplines. Given a set of DTDs and Schemas, content material that is modeled in conformance with the DTDs and Schemas can be processed by applications that are developed for these DTDs and Schemas.

A further advantage of the use of XML is the wealth of tools that are available for the processing of XML-compatible data. Of particular significance, the "Extensible Stylesheet Language" (XSL) is a language for expressing stylesheets, and the "XSL Transformations" (XSLT) is a language for transforming XML documents into other XML documents. A stylesheet contains a set of template rules, which are used to match a pattern to a source document, or "source tree" and, when the appropriate match is found, to instantiate a template to a result document, or "result tree". In this manner, XML information that is structured for one application can be relatively easily transformed into a different structure for another application.

As has become apparent from a variety of showcases like scientific assemblies and annual meetings of the Radiology Society of North America (RSNA), annual conferences and exhibitions of Healthcare Information and Management Systems Society (HIMSS), and various channels like technical conferences, standardization working group meetings, a large number of vendors have been doing encoding of DICOM SR in the XML since the DICOM SR was standardized in 2001 followed by a number of SR template supplements being developed.

Accordingly, with the extensive use of XML in representing DICOM SR reports, especially when SR Templates are used in generating a variety of SR XML documents, validation of SR XML documents against the SR templates becomes more and more important in promoting their precision, usage, and interoperability.

The constraints in SR Templates are complicated, making it a challenging task to validate SR documents against the SR Templates.

Validation of an XML document is considered at two levels: syntactic validation and semantic validation. Syntactic validation is mainly to check the structures of an XML document against its XML Schema or DTD. Semantic validation, on the other hand, mainly checks the non-structural constraints, in most cases, the content of an XML document. We already have XML schemas for the general SR Information Object Definitions (IODs). They can be used to validate the basic structures, DICOM tag information, and data types of SR XML documents.

We also have a mechanism to generate XML schemas for SR Templates. XML Schema can express the static or fixed value constraints specified in SR Templates. However, the dynamic value constraints and inter-relationship constraints specified in SR Templates cannot be expressed in W3C XML Schema 1.0. They are again highlighted below:

The Relation with Parent constraints;
The Context Group reference constraints;
The Parameter constraints; and
The Conditions (like the IFF statement and free text).

Therefore, XML schemas of either the general SR or the Templates cannot validate SR documents against the constraints specified in the SR Templates. Semantic validation is needed to accomplish this task.

Several approaches have been proposed for semantic validation like Schematron and XincaML. One of the drawbacks of these solutions is that they cannot deal with the Parameters that are often used in SR Templates. We propose an approach of using XSLT—an XML technology from the W3C for doing semantic validation of SR XML documents against the SR Templates. XSLT was developed originally for transforming an XML document to another XML document. It supports parameterized XSLT templates besides XPath. The document function allows access to external XML documents other than the source document. These features are exactly those needed to deal with Parameter, Context Group reference, and Relation with Parent constraints. Another benefit is that the results can be represented in XML so that it also makes the validation results human readable.

Characteristics of SR Templates

"Templates are patterns that specify the Concept Names, Requirements, Conditions, Value Types, Value Multiplicity, Value Set restrictions, Relationship Types and other attributes of Content Items for a particular application."[2] Templates are used to put additional constraints on an SR content tree (FIG. 1) to promote common formats and vocabularies for specific reporting applications. Templates specify not only what Content Items are required or optional but also what constraints are for Concept Names or Value Set Constraints, etc. Table 1 through Table 4 illustrates the complexity of SR Templates and how they work together to constrain SR documents. See: DICOM Supplement 26: OB-GYN Ultrasound Procedure Reports, Draft Final Text, Jan. 24, 2003, NEMA, Rosslyn, Va.

A template table has the same structure. A row number denotes each row of a Template Table. The first row is numbered 1 and subsequent rows are numbered in ascending order with increments of 1. This number denotes a row for convenient description as well as reference in conditions. The nesting level (NL) of Content Items is denoted by ">" symbols, one per level of nesting below the initial Source Content Item (of the Template). Relationship Type and Relationship Mode (Rel with Parent) constraints, if defined, are specified in this field. The Value Type field specifies the SR Value Type of the Content Item or conveys the word "INCLUDE" to indicate that another Template is to be included.

Any constraints on Concept Name are specified in this field as defined or enumerated coded entries, or as baseline or defined context groups. The VM field indicates the number of times that either a Content Item of the specified pattern or an included Template may appear in this position. The Requirement Type field specifies the requirements on the presence or absence of the Content Item or included Template. The Condition field specifies any conditions upon which presence or absence of the Content Item or its values depends. This field specifies any Concept Name(s) or Values upon which there are dependencies. Value Set Constraints, if any, are specified in this field as defined or enumerated coded entries, or as baseline or defined context groups.

BRIEF DESCRIPTION OF TABLES

Table 1 shows a TID 5000, Ultrasound Procedure Report Template.

Table 2 shows a TID 5006, Fetal Long Bones Section.

Table 3 shows an example of a TID 5008, Fetal Biometry Group.

Table 4 shows an example of TID 300 Measurement

TABLE 1

| NL | Rel with Parent | Value Type | Concept Name | VM | Req Type | Condition | Value Set Constraint |
|---|---|---|---|---|---|---|---|
| 1 | | CONTAINER | EV (125000, DCM, "OB-GYN Ultrasound Procedure Report") | 1 | M | | |
| 2 | > HAS CONCEPT MOD | INCLUDE | DTID (1204) Language of Content Item and Descendants | 1 | U | | |
| 3 | > HAS OBS CONTEXT | INCLUDE | DTID (1001) Observation Context | 1 | M | | |
| 4 | > CONTAINS | INCLUDE | DTID (5001) Patient Characteristics | 1 | U | | |
| 5 | > CONTAINS | CONTAINER | DT (111028, DCM, "Image Library") | 1 | U | | |
| 6 | >> CONTAINS | IMAGE | No purpose of reference | 1 – n | M | | |
| ... | | | | | | | |
| 10 | > CONTAINS | INCLUDE | DTID (5006) Long Bones Section | 1 – n | U | | |
| ... | | | | | | | |
| 17 | > CONTAINS | INCLUDE | DTID (5013) Follicles Section | 1 | U | | $Laterality = EV (G-A101, SRT, "Left") $Number = EV (11879-4, LN, "Number of follicles in left ovary") |

TABLE 1-continued

| | Rel with NL Parent | Value Type | Concept Name | VM | Req Type | Condition | Value Set Constraint |
|---|---|---|---|---|---|---|---|
| 18 | > CONTAINS | INCLUDE | DTID (5013) Follicles Section | 1 | U | | $Laterality = EV (G-A100, SRT, "Right") $Number = EV (11880-2, LN, "Number of follicles in right ovary") |

Table 1 is the template for the root of the content tree for the OB-GYN ultrasound procedure report.

Referring to Table 1, each reporting application has one and only one root Template. This root Template invokes one or more sub Templates. All the Templates are represented in the table format with the same number of columns. The Rel with Parent column specifies the relationship of the Content Item with its parent. The Value Type column constrains the content type of the Content Item. If the value of this column is 'INCLUDE', it means that another Template is invoked. The Concept Name column specifies the coded concept of the Content Item. Table 1 is the root SR Template of OB-GYN Ultrasound Procedure Report. Row 1 of Table 1 defines the constraints on the Root Content Item (See FIG. 1) that is mandatory (M) without a relationship constraint. The other rows may invoke other sub Templates like TID 5006 (See Table 2) to further constrain sub Content Items.

passed from its invoker, Row 10 of Table 1. There are three types of constraints for Concept Name and Value Set Constraint: Coded Concept, Context Group reference, and Parameter. A Coded Concept is basically a coded vocabulary like DT (125005, DCM, "Biometry Group") in row 1 of Table 3 or EV (18185-9, LN, "Gestational Age") in row 3 of Table 3. Here, DT stands for defined terms, and EV for enumerated values. The three values within the brackets are Code Value (CV), Coding Scheme Designator (CSD), and Code Meaning (CM). A Context Group reference is comprised of a Context Group type and an identifier (ID) number like DCID (228) in row 4 of Table 3. DCID stands for defined context group identifier. A Context Group contains a group of coded concepts or other Context Group references. In this case, the Concept Name or Value Set Constraint is limited to one of the Coded Concepts given in a referenced Context Group. We call them static value constraints if the

TABLE 2

| | Rel with NL Parent | VT | Concept Name | VM | Req Type | Condition | Value Set Constraint |
|---|---|---|---|---|---|---|---|
| 1 | | CONTAINER | DT (125003, DCM, "Fetal Long Bones") | 1 | M | | |
| 2 | > HAS OBS CONTEXT | INCLUDE | DTID (1008) Subject Context, Fetus | 1 | MC | IF this template is invoked more than once to describe more than one fetus | |
| 3 | > CONTAINS | INCLUDE | DTID (5008) Fetal Biometry Group | 1 – n | M | | $BiometryType = MemberOf {DCID (12006) Fetal Long Bones Biometry Measurements} |

Table 2, a Long Bones template is a container for biometric data of long bones.

Referring to Table 2, the first cell of the Rel with Parent column of Table 2 is blank. Its actual value is CONTAINS constraints are given as fixed values like CONTAINER for Value Type and DT (125003, DCM, "Fetal Long Bones") for Concept Name. We call them dynamic value constraints if they are given as a Context Group Reference or Parameter.

TABLE 3

| | Rel with NL Parent | Value Type | Concept Name | VM | Req Type | Condition | Value Set Constraint |
|---|---|---|---|---|---|---|---|
| 1 | | CONTAINER | DT(125005, DCM, "Biometry Group") | 1 | M | | |
| 2 | > CONTAINS | INCLUDE | DTID (300) Measurement | 1 – n | MC | At least one of row 2 and 3 shall be present | $Measurement = $BiometryType $Derivation = DCID (30627) Measurement Type |
| 3 | > CONTAINS | NUM | EV (18185-9, LN, "Gestational Age") | 1 | MC | At least one of row 2and 3 shall be present | Units = EV (d, UCUM, days) |
| 4 | >> INFERRED FROM | CODE | DCID (228) Equation or Table | 1 | U | | DCID (12013) Gestational Age Equations and Tables |

Table 3, a Biometry Group template is container for a biometric value and its associated growth metrics.

A Parameter declared in a Template conveys a value passed from the invoking Template. The passed value can be a Coded Concept like EV (G-A101, SRT, "Left") in row 17 of Table 1, a Context Group reference like DCID (3627—Measurement Type) in row 2 of Table 3, or another Parameter like Biometry Type in row 2 of Table 3. From row 3 of Table 2 to row 2 of Table 3, and then to row 1 of Table 4 illustrates how Context Group reference DCID (12006—Fetal Long Bones Biometry Measurement) is passed from TID 5006 (Table 2) to the parameter Biometry Type declared in TID 5008 (Table 3), and then to the parameter Measurement declared in TID 300 (Table 4).

TABLE 4

| NL | Rel with Parent | Value Type | Concept Name | VM | Req Type | Condition | Value Set Constraint |
|---|---|---|---|---|---|---|---|
| 1 |  | NUM | $Measurement | 1 | M |  | Units = $Units |
| 2 | > HAS CONCEPT MOD | CODE | $ModType | 1 – n | U |  | $ModValue |

This Template provides the properties of a numeric measurement, including evaluations of its normality and/or significance, its relationship to a reference population, and an indication of its selection from a set of measurements.

VM and Req Type constrain the number of occurrences and the mandatoriness of the Content Item specified in a row.

When the Req Type is Conditional like C, MC, or UC, there is a condition statement expressed as logical OR, or XOR, IF and only IF (IFF), or free text like that in row 2 of Table 2. We call this type of constraints inter-relationship constraints.

SUMMARY OF THE INVENTION

A first objective of the present invention, therefore, is to provide a method, framework and system using XSLT technology to generate XSLT stylesheets that facilitate the validation of SR XML documents.

A second objective of the present invention is to provide a method, framework and system for using XSLT technology to validate SR XML documents.

These objectives and others are achieved by providing a method to validate SR XML documents using XLST technology alone or as a complement to XML Schema. A framework of generating XSLT stylesheets is provided. The test results show that XSLT can complement XML Schema in XML document validation.

Although XML may be considered a relatively new and specialized language, it can be expected that more programmers and other computer professionals will be familiar with XML than those who are familiar with DICOM. Additionally, it can be expected that more general-purpose utilities and applications will be available for use on XML encoded information than will be available for use on DICOM SR encoded information.

A preferred method, framework and system for validating a DICOM SR XML document, can include: selecting an XML schema of DICOM SR IOD (Information Object Definitions), followed by selecting an XML parser to perform syntactic validation, followed by determining which DICOM SR template is used, followed by selecting an XSLT processor to perform semantic validation, and then generating validation result in XML.

A method, framework, and system of generating XSLT stylesheets from XML representation of DICOM SR templates, can include selecting an XML representation of DICOM SR template, then selecting an XSLT style sheet of generating XSLT style sheets from XML representation of DICOM SR templates, then selecting an XSLT processor to perform generating an XSLT stylesheet of validating a DICOM SR template constraints.

A method, framework and system of developing XSLT stylesheets for generating XSLT stylesheets from XML representation of DICOM SR templates, can include determining whether the DICOM SR template is a root template or not, if root template, first generating the stylesheet inclusions for the all the invoked XSLT templates of the sub DICOM SR templates; then generating a named XSLT template, if not root template, then generating a named XSLT template with XSLT template parameters for sub DICOM SR template parameters, followed by generating an anonymous XSLT template for DICOM SR template rows in the top or same level which performs passing template parameters if existing, checking the requirements of these rows, and validating the content against content constraints by calling the XSLT template for a single content item, and if a DICOM SR template row has nested template row(s), repeating the preceding step.

A method, framework, and system of defining XSLT variables in representing XPath expressions of DICOM SRXML documents, can include determining which XML elements or paths in a DICOM SR XML documents have impact on pattern matching during validation, and assigning XSLT variable names, followed by determining the corresponding value or XPath of each variable in a given XML schema, and then creating an XSLT stylesheet consisting of these variables and their values.

A method, framework, and system of developing XSLT stylesheets for generating XSLT stylesheets from an XML representation of DICOM SR templates, can include determining whether each of the DICOM SR templates is a non-root template or not, if not root template, then generating a named XSLT template with XSLT template parameters for sub DICOM SR template parameters, followed by generating an anonymous XSLT template for DICOM SR template rows in the top or same level which performs passing template parameters if existing, checking the requirements of these rows, and validating the content against content constraints by calling the XSLT template for a single content item or a sub SR template using a template caller, if a DICOM SR template row has nested template row(s), repeat preceding step, generating template callers based on the type of a DICOM SR template row, if a single content item, the caller invokes an XSLT template for content item validation, if a sub DICOM SR template, the caller invokes an XSLT template for DICOM SR sub template validation with parameters, and if a composite content item having nested content items, the caller invokes an XSLT template for the current level content item and also invokes XSLT template for nested SR content item validation.

A method, framework and system of developing XSLT stylesheets for generating XSLT stylesheets for validating content items, can include creating an XML document which includes a set of parameters used for content item validation; the numbers and names of these parameters are determined based on what type of content item, followed by developing an XSLT stylesheet to transform the XML document to an XSLT stylesheet.

Further objects and advantages of this invention will be apparent from the following detailed description of the presently preferred embodiments that are illustrated schematically in the accompanying drawings.

DESCRIPTION OF THE PREFERRED EMBODIMENTS

Before explaining the disclosed embodiments of the present invention in detail it is to be understood that the invention is not limited in its application to the details of the particular arrangements shown since the invention is capable of other embodiments. Also, the terminology used herein is for the purpose of description and not of limitation.

Figure 1:
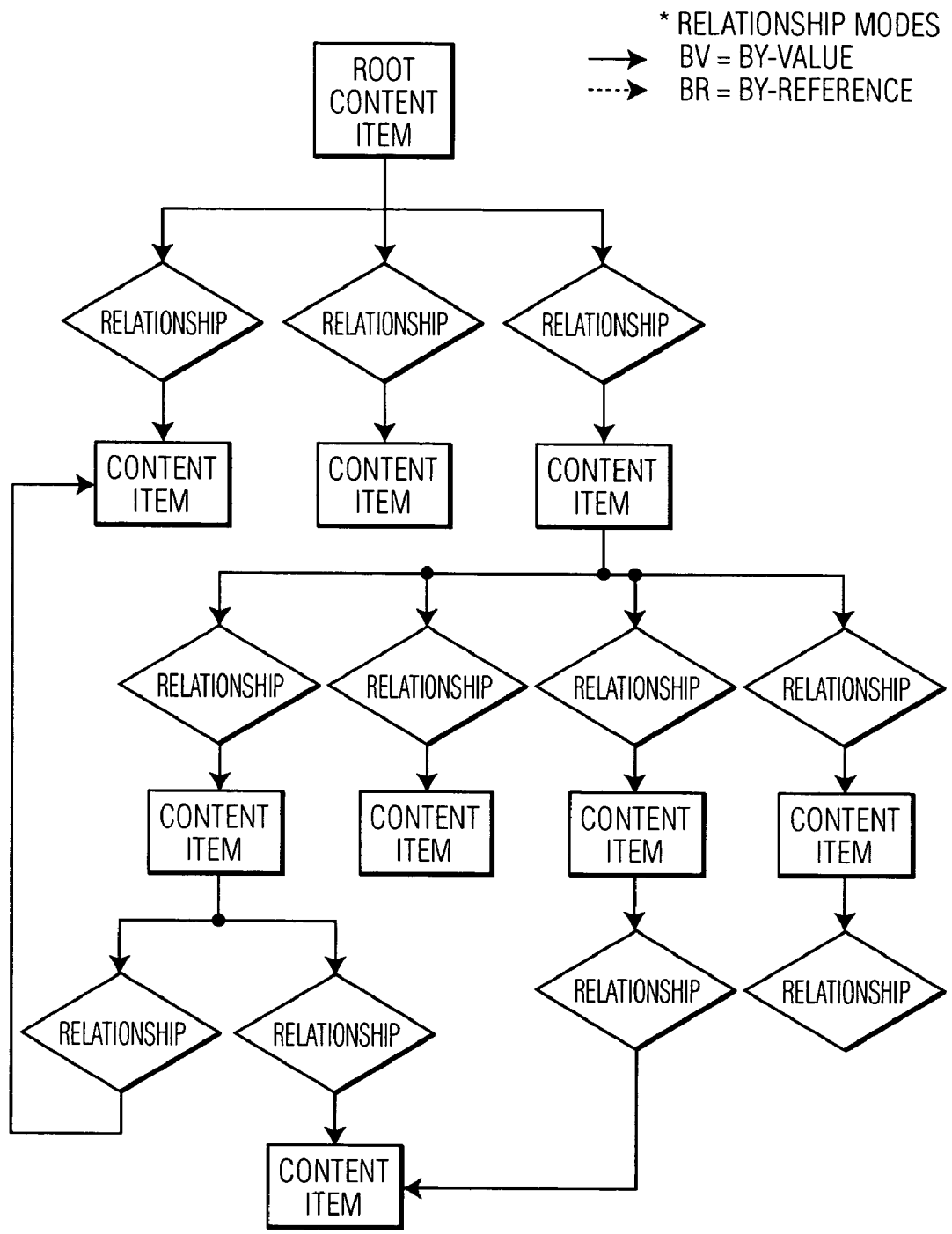
FIG. 1 shows the Scenarios of validating SR XML documents.
Figure 2:
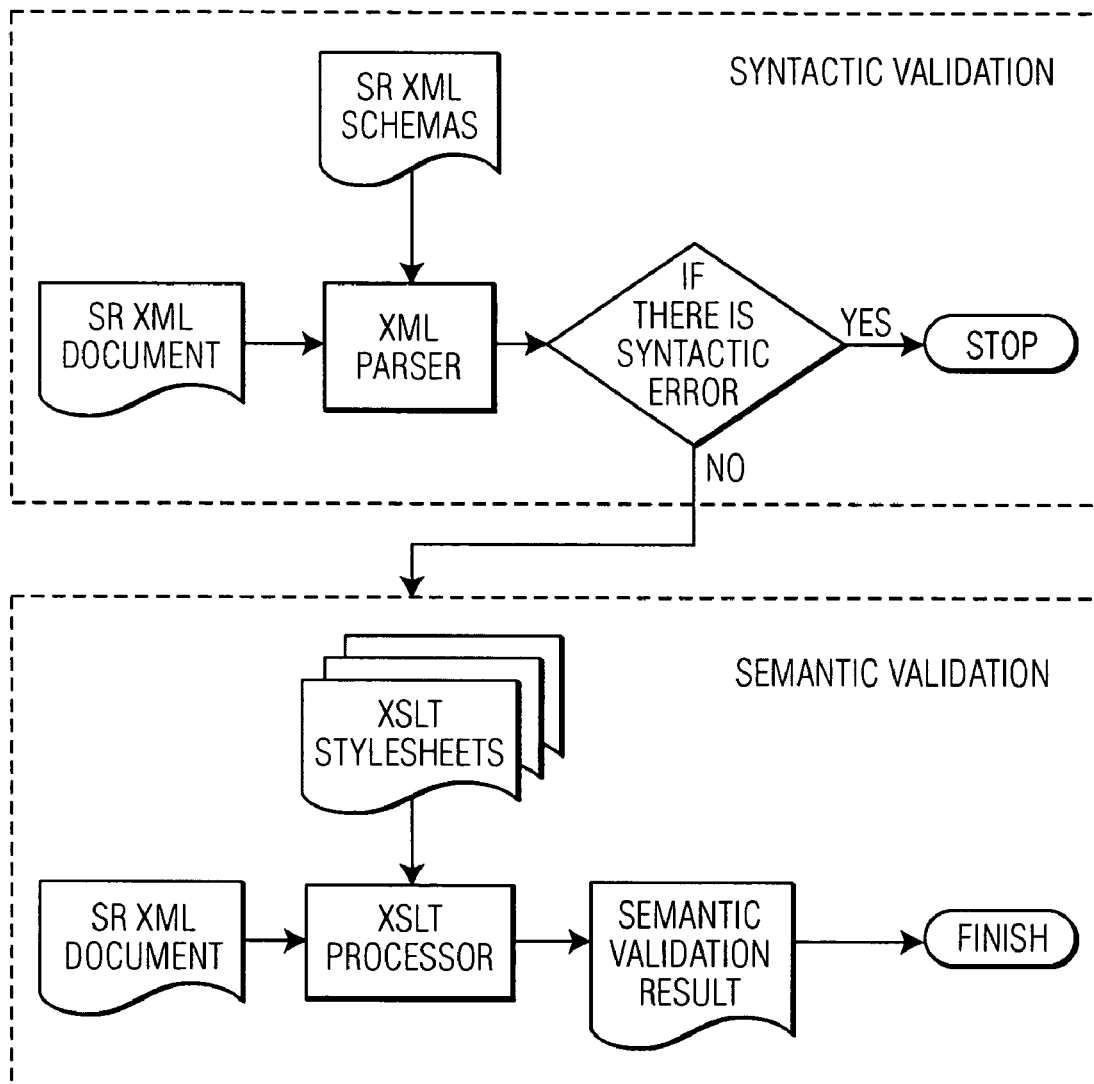
FIG. 2 illustrates shows the flowchart of validating SR XML documents.

Flowchart of Validating SR XML Documents (FIG. 2)

The workflow of validating SR documents is shown in FIG. 2. The syntactic validation of SR XML documents against SR XML schemas is executed in the first step. If there are any syntactic errors, the validation process stops. Otherwise, the semantic validation of SR XML documents against the SR Templates is performed. The flowchart of validating SR documents is shown is FIG. 2.

In the first step, syntactic validation checks the structures, DICOM tag information, and data types of an SR XML document using any Schema-supported XML parser together with a predefined SR XML schema. In the second step, it validates an SR XML document against the constraints specified in the SR Templates of a specific reporting application by using an XSLT processor together with a set of XSLT stylesheets. The key part in this step is the XSLT stylesheets.

Figure 3:
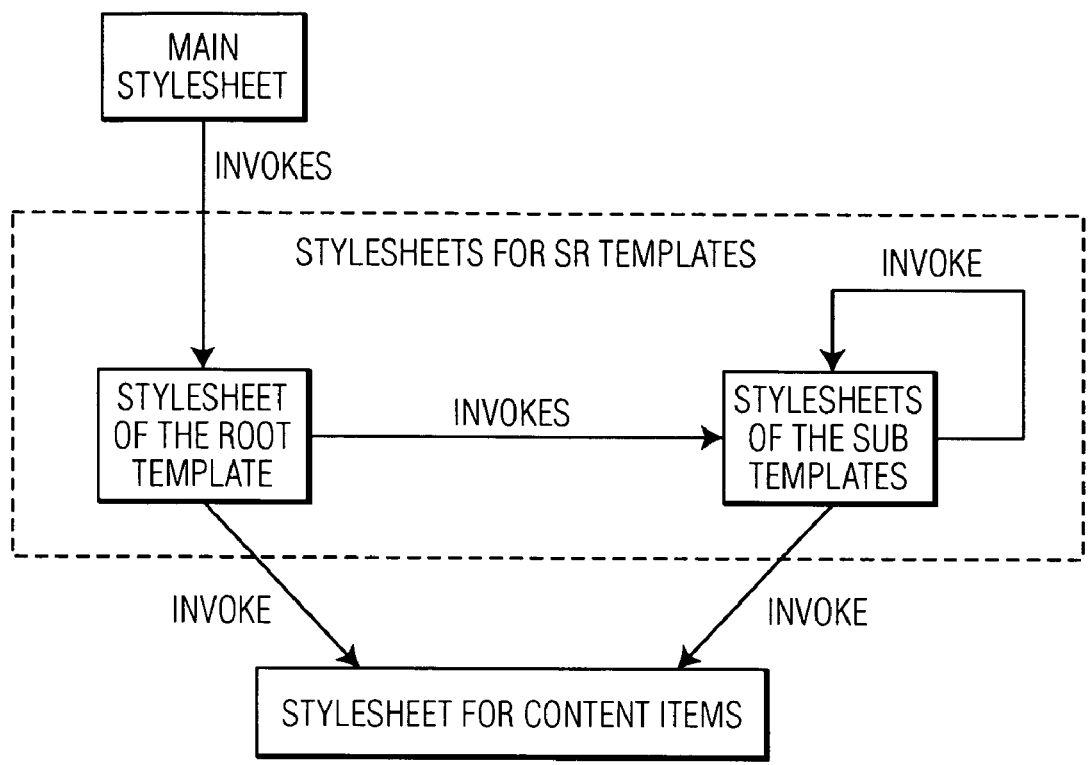
FIG. 3 shows the relationships of Different Stylesheets.

Overview of Stylesheets (FIG. 3)

Figure 4:
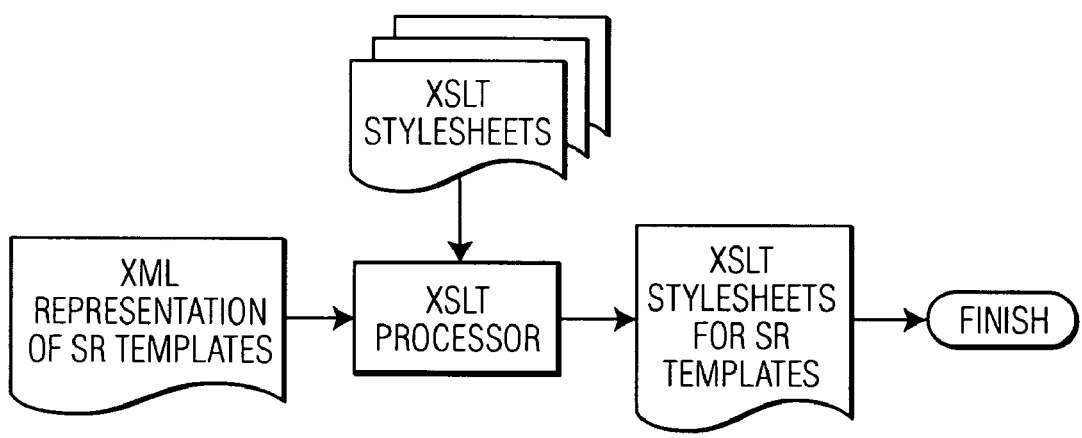
FIG. 4 illustrates an example of a block of OB-GYN SR XML instance.

Referring to FIGS. 3-4, the XSLT stylesheets for SR document validation are divided into three parts in terms of their functions: main stylesheets, stylesheets for SR Templates, and the stylesheet for Content Items.

The main stylesheet invokes the stylesheet of the root SR Template. The latter invokes one or more stylesheets of the sub SR Templates. A stylesheet for a sub Template may invoke one or more stylesheets for other sub SR Templates. The stylesheets for SR Templates invokes the stylesheet for Content Items.

A complete SR XML document includes Patient, Study, Series, Equipment, and Document module related information. SR Templates only specify constraints on Content Items that belong to the SR Document Content Module. Therefore, the main stylesheet selects the element sr_document_content_module and invokes the XSLT template of the root SR Template (see Listing 1 as an example). tid_5000_validation is the main template of the stylesheet, tid_5000_validation-.xsl, of the root Template-OB-GYN Ultrasound Procedure Report.

Listing 1 Main XSLT Stylesheet for Validating SR Document Content Module

```
<xsl:stylesheet xmlns:xsl="http://www.w3.org/1999/XSL/Transform"
    xmlns:pms="http://www.philips.com/pms" version="1.0">
    <xsl:output indent="yes"/>
    <xsl:variable name="Debug">false</xsl:variable>
    <xsl:include href="sup-26/tid_5000_validation.xsl"/>
    <xsl:template match="/">
        <xsl:apply-templates select="pms:sr_document_content_module"/>
    </xsl:template>
    <xsl:template match="pms:sr_document_content_module">
        <SR_validation>
            <xsl:call-template name="tid_5000_validation"/>
        </SR_validation>
    </xsl:template>
</xsl:stylesheet>
```

In order to invoke the external template, tid_5000_validation, the stylesheet tid_5000_validation.xsl, containing such a template must be included. For the purpose of tracing the test results, a variable Debug is defined. If its value is true, the validation result reports both valid and invalid content (see part of the validation result in Listing 2-3). If its value is false, the validation result only reports invalid content (see part of the validation result in Listing 2-3). The template tid_5000_validation is generated from the XML representation of the SR Template TID 5000.

The main stylesheet is very straightforward and easy to create either manually or automatically.

The XSLT stylesheets for SR Templates are the major part of stylesheets for SR document validation. Each of them checks if the mandatory Content Items are missing and invokes either the templates of other sub SR Templates or the templates for Content Items. Listing 2 illustrates how tid_

5000_validation template invokes CONTAINER_content_item_validation template and tid_5013_validation template of SR Template TID 5013.

Listing 2 A Portion of tid_5000_validation Stylesheet

```
<xsl:template name="tid_5000_validation">
    <tid_5000>
        ...
        <xsl:when test="normalize-space(document_content_macro/concept_name_code_sequence
/concept_name_code_sequence_item/code_sequence_macro/code_value)='125000'">
            <xsl:call-template name="CONTAINER_content_item_validation">
            ...
            </xsl:call-template>
            <xsl:apply-templates select="document_relationship_macro/content_sequence"
mode="tid_5000_row_1"/>
        </xsl:when>
        ...
    </tid_5000>
</xsl:template>
<xsl:template match="document_relationship_macro/content_sequence" mode="tid_5000_row_1">
    ...
    <xsl:for-each select="content_sequence_item">
        ...
        <xsl:when test="normalize-space(document_content_macro/concept_name_code_sequence
/concept_name_code_sequence_item/code_sequence_macro/code_value)='121070' and ...">
            <xsl:call-template name="tid_5013_validation">
            ...
            </xsl:call-template>
        </xsl:when>
        ...
    </xsl:for-each>
</xsl:template>
```

The complexity of SR Templates makes it difficult to create these XSLT templates. It is possible to manually generate them by going through row by row from one Template table to another. This will be very time consuming and error-prone. Automation of this generation process is no doubt a better way to go. We use XSLT technology to realize this task.

The XSLT stylesheet for Content Item validation contains a template for each Content Item. They are independent of SR Templates. Each of them validates Relationship Type, Value Type, and Coded Concepts of a particular type of Content Item in an SR document against the given values in the corresponding Template. Those given values are passed from the caller of an XSLT template of Content Item through the template parameters. Listing 3 demonstrates how a CONTAINER Content Item is validated. The templates also share the templates relationship_type_validation, value_type_validation, and concept_name_code_validation for other Content Items.

Listing 3 CONTAINER_content_item_validation Stylesheet

```
<xsl:template name="CONTAINER_content_item_validation">
    ...
    <xsl:call-template name="relationship_type_validation">
    ...
    </xsl:call-template>
    <xsl:call-template name="value_type_validation">
    ...
    </xsl:call-template>
    <xsl:call-template name="concept_name_code_validation">
    ...
    </xsl:call-template>
</xsl:template>
```

Framework of XSLT Stylesheet Generation

Figure 7:
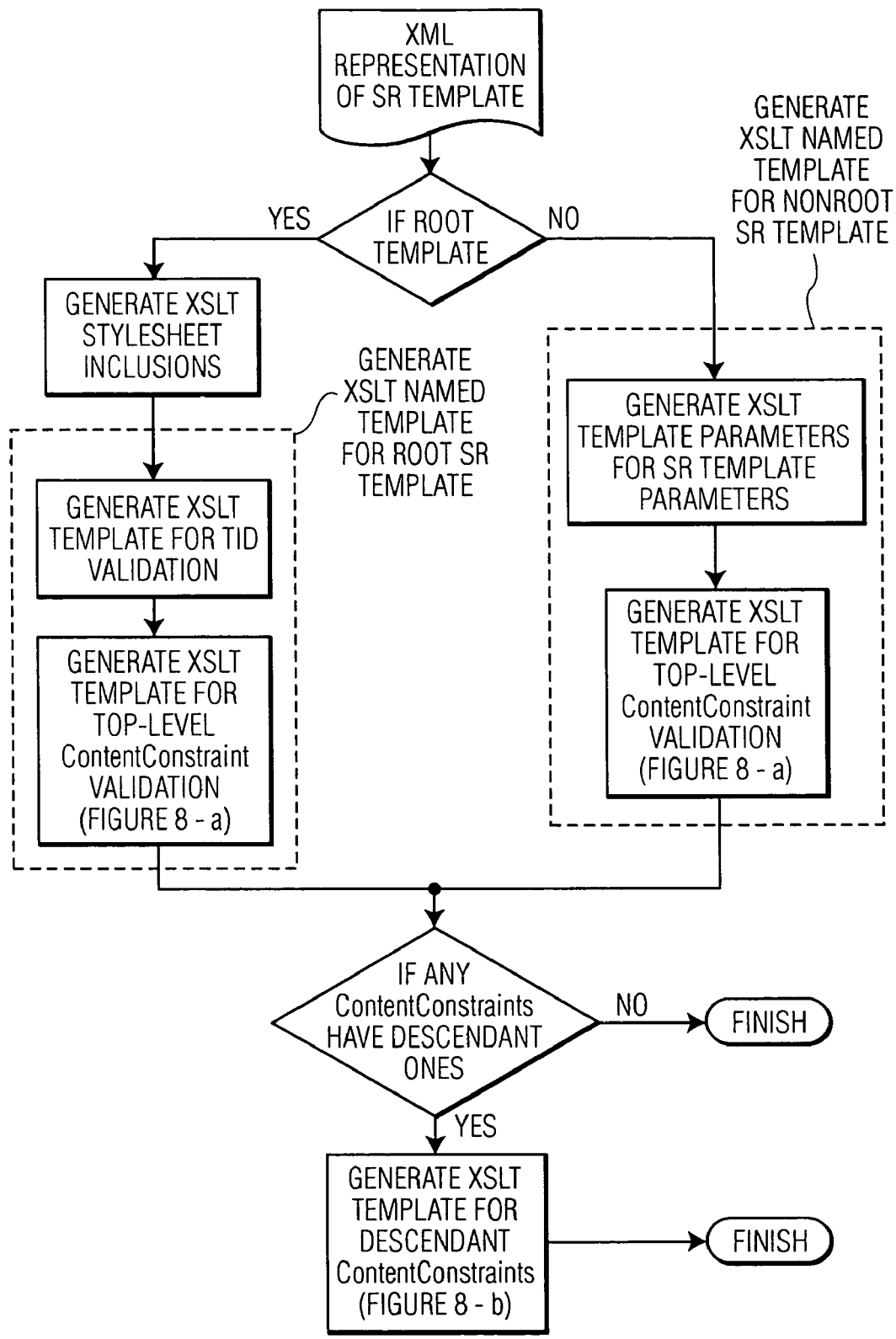
FIG. 7 illustrates the main process of generating XSLT stylesheets.

Referring to FIG. 7, we use XSLT technology to generate XSLT stylesheets of SR Templates for SR document validation. The input is the XML representation of SR Templates. Any XSLT processor can be used. What we need is to implement a set of XSLT stylesheets for this transformation.

XML Representation of SR Templates

Figure 5:
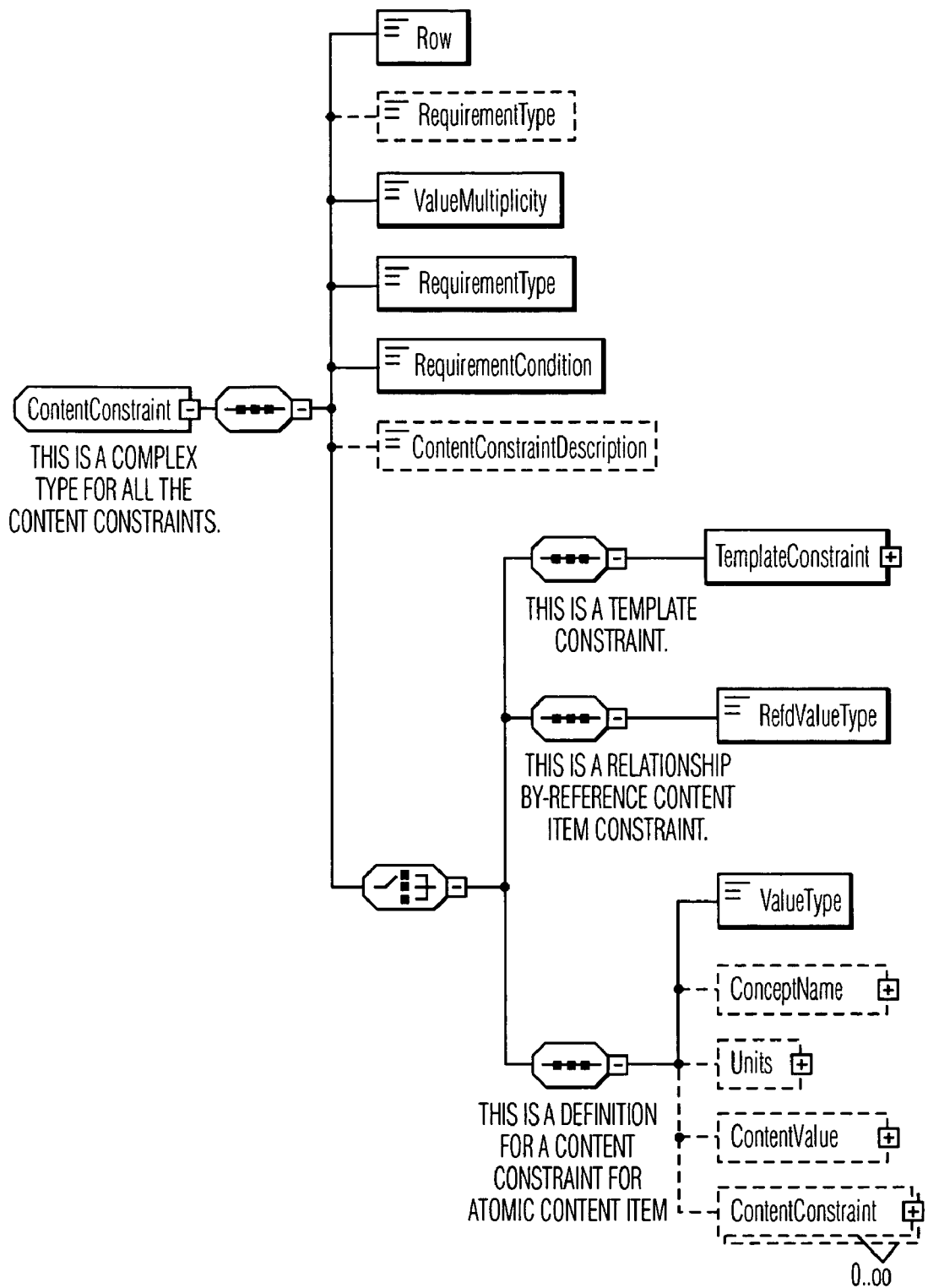
FIG. 5 shows the graphical diagram of XML Schema of SR Templates.

Currently the rich structure of SR in general and Templates in particular are described using tables. Errors and inconsistencies frequently happen when the specification is being developed or updated since tables are insufficient to capture adequately the internal structure of SR Templates. To address this problem a UML model has been proposed as the information model for SR Templates. From this UML model we have developed an XML representation of SR Templates (see FIG. 5) and also an XML representation of Context Groups (see FIG. 6).

DicomSRTemplate is the root element. Title and TID are the main meta-data of SR Template. RootConstraint indicates if a Template is a root one or not. DeclaredParameter represents a Template parameter. A ContentConstraint holds all the constraints of a single row in a Template table. It has child ContentConstraint element(s) if a row in a Template table has nested rows like row 5 in Table 1. Row represents the first column of Template Table. RelationshipType represents the third row, ValueMultiplicity represents the sixth, RequirementType represents the seventh, and RequirementCondition represents the eighth. If the value of ValueType (fourth column) is INCLUDE, TemplateConstraint must be present. If the Relationship is by-reference type, i. e, the value of Rel With Parent (third column) starts with 'R-', RefdValueType must be present. Otherwise, ValueType is present together with ConceptName (fifth column), and/or Units, and/or ContentValue, and/or ContentConstraint (ninth column). Listing 4 gives a portion of the XML representation of the root Template TID 5000.

Listing 4 A portion of XML Representation of Template TID 5000

```
<DicomSRTemplate>
    <Title>OB-GYN Ultrasound Procedure Report</Title>
    <TID>5000</TID>
    <RootConstraint>true</RootConstraint>
    <Extensibility>EXTENSIBLE</Extensibility>
    <ContentConstraint>
        <Row>1</Row>
        <ValueMultiplicity>1</ValueMultiplicity>
        <RequirementType>M</RequirementType>
        <RequirementCondition/>
        <ValueType>CONTAINER</ValueType>
        <ConceptName>
            <CodeValueConstraint>
            ...
            </CodeValueConstraint>
        </ConceptName>
        <ContentConstraint>
            <!-- Row 2 information -->
        </ContentConstraint>
        <!-- Row 3 to Row 4 ... -->
        <ContentConstraint>
            <Row>5</Row>
            ...
            <ConceptName>
                <!-- CodeValueConstraint -->
            </ConceptName>
            <ContentConstraint>
                <Row>6</Row>
                ...
            </ContentConstraint>
        </ContentConstraint>
        <!-- Row 7 to Row 18 ... -->
        <ContentConstraint>
</DicomSRTemplate>
```

There is one and only one top-level ContentConstraint element in a root Template, like row 1 of Table 1. The sub-level ContentConstraint elements represent the constraints from row 2 to row 18 of Table 1. A sub-level ContentConstraint element has child ContentConstraint(s) if a Template row has any nested row(s), like row 5 of Table 1 having a nested row 6. In some cases, a sub Template may have more than one top-level ContentConstraint elements.

Figure 6:
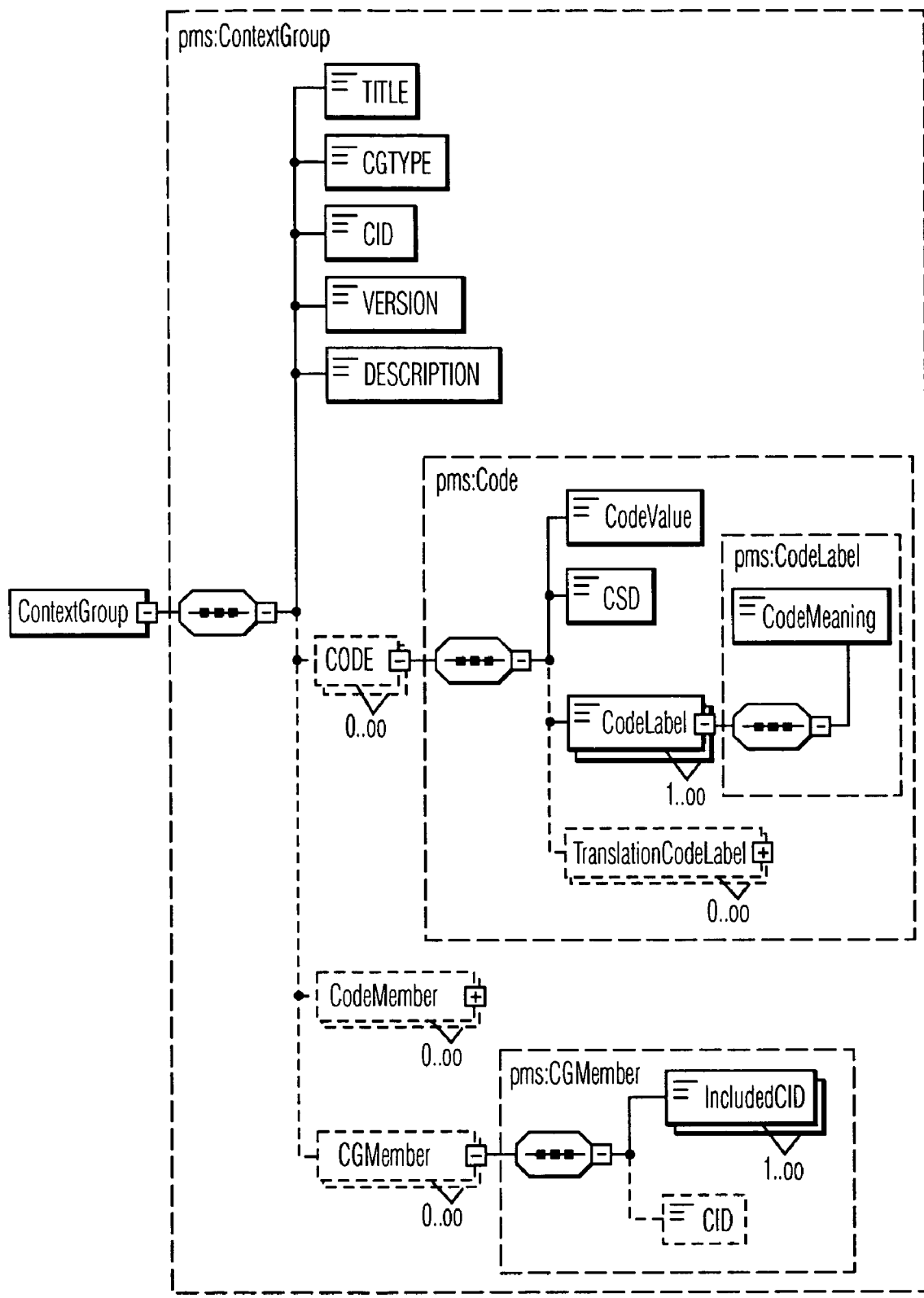
FIG. 6 shows the graphical diagram of XML Schema of context groups.

FIG. 6 represents the XML definition of Context Groups. Title, CGType, and CID are the main meta-data of Context Groups. A Context Group may have zero or more Codes and/or zero or more CGMembers. A Code defines a coded concept by giving a CodeValue (Code Value), CSD (Coding Scheme Designator), and CodeLabel holding its CodeMeaning (Code Meaning). A CGMember lists one or more IncludedCIDs (included Context Group ID). Listing 5 shows a block of the XML representation of Context Group DCID 12006— Fetal Long Bones Biometry Measurements. Such representations will be used as the input of the external source of the XSLT stylesheets for SR Templates.

Listing 5 A Block of the XML Representation of Context Group DCID 12006

```
<ContextGroup>
    ...
    <Code>
        <CodeValue>11966-9</CodeValue>
        <CSD>LN</CSD>
        <CodeLabel>
            <CodeMeaning>Humerus length</CodeMeaning>
        </CodeLabel>
    </Code>
    <Code>
        <CodeValue>11967-7</CodeValue>
        <CSD>LN</CSD>
        <CodeLabel>
            <CodeMeaning>Radius length</CodeMeaning>
        </CodeLabel>
    </Code>
    ...
    <Code>
        <CodeValue>11963-6</CodeValue>
        <CSD>LN</CSD>
        <CodeLabel>
            <CodeMeaning>Femur Length</CodeMeaning>
        </CodeLabel>
    </Code>
</ContextGroup>
```

Flowcharts of Generating the Stylesheets of Validating SR Documents

Figure 8A:
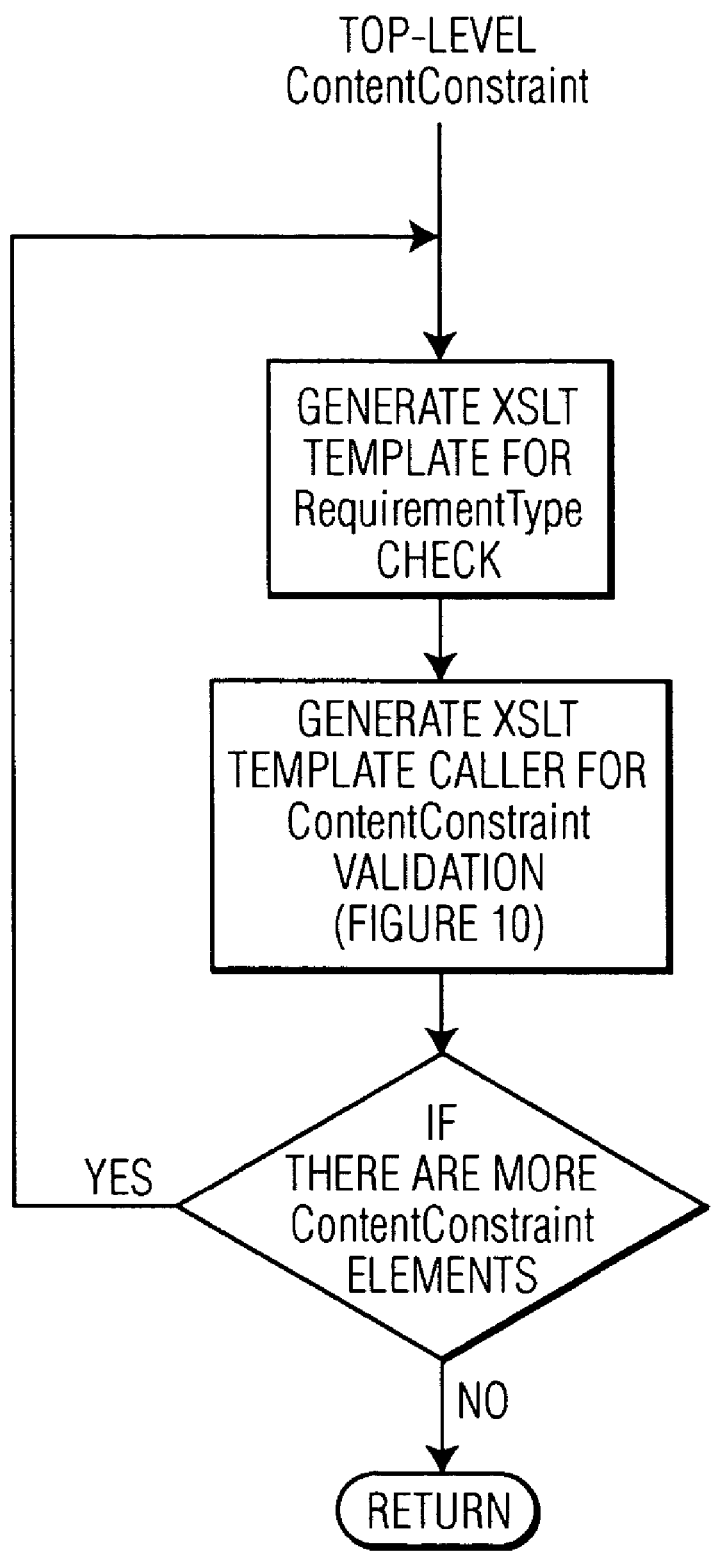
FIG. 8 illustrates processing top-level and branch-level ContentConstraints.
Figure 8B:
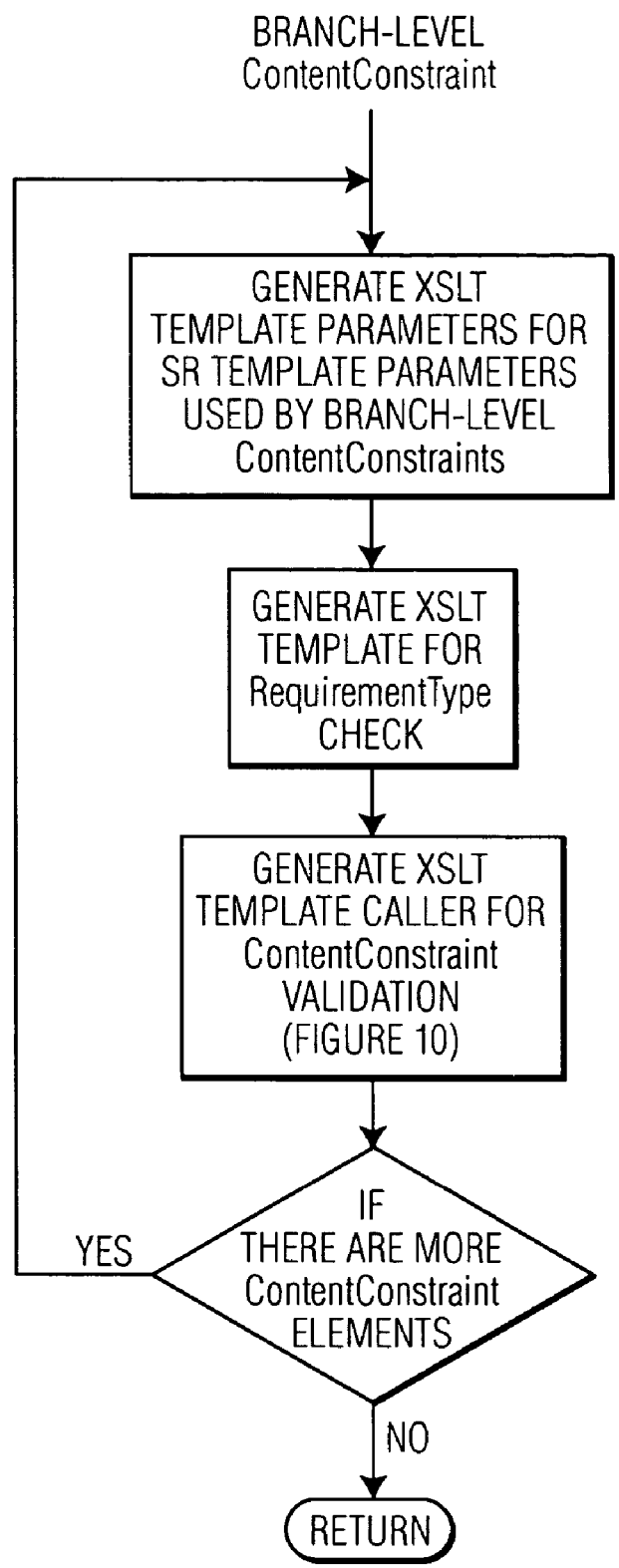
Figure 9:
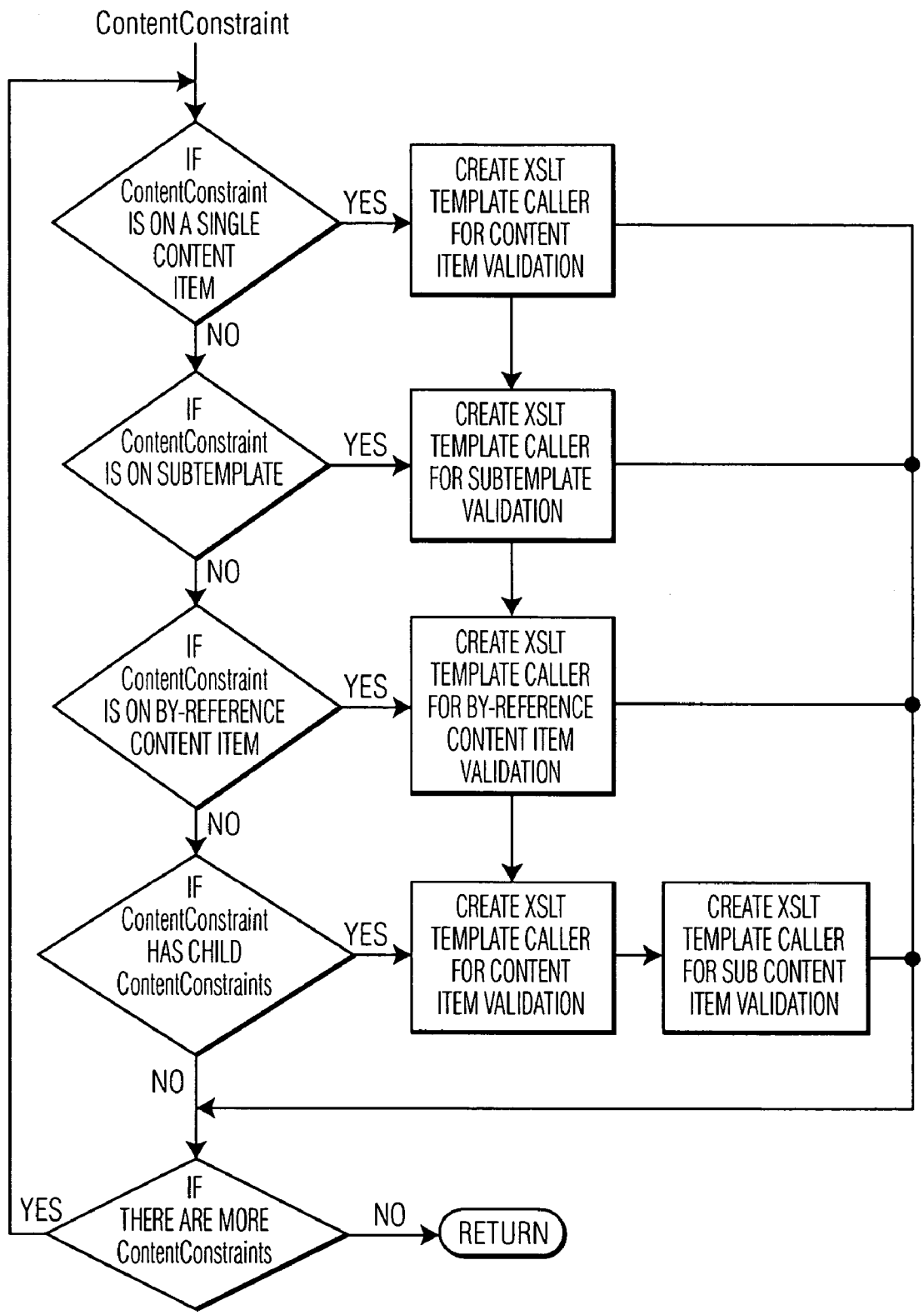
FIG. 9 illustrates the process of template caller creation.

FIGS. 7, 8 and 9 illustrate the process of generating XSLT stylesheets from the XML representation of SR Templates.

FIG. 7 shows the main process of generating XSLT stylesheets. The process starts by reading in an XML representation of an SR Template. If the processed Template is a root one, it first generates the stylesheet inclusions for the invoked templates of the sub Templates, and then creates a named XSLT template (see FIG. 8-a). If the processed Template is a non-root one, it also generates a named XSLT template with XSLT template parameters for sub SR Template parameters (see FIG. 8-a). In both cases, anonymous XSLT templates for descendant ContentConstraints are also generated (see FIG. 8-b), if such ContentConstraints exist.

FIG. 8 shows how to process top-level and branch-level ContentConstraints. For each top-level ContentConstraint, a template is generated for checking if a mandatory Content Item or sub Template is missing, and also a template caller (See FIG. 9) is generated to invoke a template for further validation. For each ContentConstraint at the same branch-level, a template caller similar to the one for the top-level ContentConstraint is created with the template parameters passing the values given in its upper level.

ContentConstraint.

As shown in FIG. 9, different template callers are created depending upon what constraint a ContentConstraint specifies, e.g., a template caller for content item validation is created if the ContentConstraint is on a single content item.

Implementation of XSLT Stylesheets

The above flowcharts are also implemented in a set of XSLT stylesheets because XSLT is a powerful technology of processing XML documents.

In order to make this approach flexible to the different Schema definitions of SR documents, a set of global XSLT variables are defined to represent the XPath expressions used in the whole validation process. Listing 6 gives these variables with the values specific to XML schemas of DICOM SR we developed. The value sets of these variables for other namespaces can be defined in the same way.

Listing 6 XSLT Variables and the Values Specific to PRB SR XML Format

```
<xsl:stylesheet version="1.0" xmlns:xsl="http://www.w3.org/1999/XSL/Transform">
    <!-- These XPath variables are PRB SR XML specific. -->
    <xsl:variable name="root_path">pms:sr_document_content_module</xsl:variable>
    <xsl:variable name="tid_path">
        document_relationship_macro/content_template_sequence/content_template_sequence_item/
        template_identification_macro/template_identifier
    </xsl:variable>
    <xsl:variable name="content_sequence_path">
        document_relationship_macro/content_sequence
    </xsl:variable>
    <xsl:variable name="content_sequence_item_path">content_sequence_item</xsl:variable>
    <xsl:variable name="relationship_type_path">relationship_type</xsl:variable>
    <xsl:variable name="value_type_path">document_content_macro/value_type</xsl:variable>
    <xsl:variable name="concept_name_code_sequence_item_path">
        document_content_macro/concept_name_code_sequence/
        concept_name_code_sequence_item
    </xsl:variable>
    <xsl:variable name="concept_name_code_value_path">
        document_content_macro/concept_name_code_sequence/
        concept_name_code_sequence_item/code_sequence_macro/code_value
    </xsl:variable>
    <xsl:variable name="concept_code_sequence_item_path">
        document_content_macro/code_macro/concept_code_sequence/
        concept_code_sequence_item/code_sequence_macro
    </xsl:variable>
    <xsl:variable name="concept_code_value_path">
        concept_code_sequence/concept_code_sequence_item/
        code_sequence_macro/code_value
    </xsl:variable>
    <xsl:variable name="numeric_measurement_path">
        numeric_measurement_macro/measured_value_sequence
    </xsl:variable>
    <xsl:variable name="measurement_units_sequence_item_path">
        numeric_measurement_macro/measured_value_sequence/
        measured_value_sequence_item/measurement_units_code_sequence/
        measurement_units_code_sequence_item</xsl:variable>
    <xsl:variable name="person_name_path">person_name</xsl:variable>
    <xsl:variable name="date_path">date</xsl:variable>
    <xsl:variable name="time_path">time</xsl:variable>
    <xsl:variable name="datetime_path">date_time</xsl:variable>
    <xsl:variable name="text_value_path">text_value</xsl:variable>
    <xsl:variable name="uid_path">uid</xsl:variable>
    <xsl:variable name="image_reference_path">
        image_reference_macro/composite_object_reference_macro/
        referenced_sop_sequence
    </xsl:variable>
    <xsl:variable name="waveform_reference_path">
        waveform_reference_macro/composite_object_reference_macro/
        referenced_sop_sequence
    </xsl:variable>
    <xsl:variable name="composite_object_reference_path">
        composite_object_reference_macro/referenced_sop_sequence
    </xsl:variable>
    <xsl:variable name="temporal_coord_path">
        temporal_coordinates_macro/temporal_range_type
    </xsl:variable>
    <xsl:variable name="spatial_coord_path">
        spatial_coordinates_macro/graphic_type
    </xsl:variable>
    <xsl:variable name="referenced_content_item_id_path">
        referenced_content_item_identifier
    </xsl:variable>
    <xsl:variable name="code_value_path">code_value</xsl:variable>
    <xsl:variable name="csd_path">coding_scheme_designator</xsl:variable>
    <xsl:variable name="code_meaning_path">code_meaning</xsl:variable>
</xsl:stylesheet>
```

Each variable element specifies a name of the variable and the value of this variable.

Main XSLT Stylesheet

As previously described earlier, it can be manually created or mechanically generated. The function of main stylesheets is to invoke a corresponding XSLT template for a specific SR Templates, see a sample XSLT template in Listing 1.

XSLT Stylesheets for Content Item Validation

An SR Template specifies the value constraints on Content Items but not on the structure of Content Items. These values can be passed through template parameters. The templates for validating Content Items of SR documents can be shared by all the stylesheets of SR Templates no matter what reporting applications.

A main XSLT template is created for each type of Content Items. In order to make these templates reusable and flexible for different XML representations of SR documents, and to avoid having error-prone and inconsistent code, we use XSLT to generate these templates. First of all, we create an XML instance that contains all the parameters of each Content Item type. Then, we implement an XSLT stylesheet for generating the stylesheet for validating Content Items of SR documents.

An XML document is created including the parameters to be used for Content Item validation. For instance, an element content_item_type with an id of CODE has 10 parameters,

```
<content_item_type id="CODE">
    <parameter>RelationshipType</parameter>
    <parameter>ValueType</parameter>
    <parameter>CodeValue</parameter>
    <parameter>CSD</parameter>
    <parameter>CodeMeaning</parameter>
    <parameter>ConceptName</parameter>
    <parameter>CVCodeValue</parameter>
    <parameter>CVCSD/parameter>
    <parameter>CVCodeMeaning</parameter>
    <parameter>ConceptCode</parameter>
</content_item_type>
``` id tells what type of Content Item. The parameter RelationshipType holds the value of Relationship Type passed from the template caller; ValueType holds the value of Value Type passed from the template caller; CodeValue, CSD, and CodeMeaning hold the EV or DT value of Concept Name of CODE passed from the template caller; ConceptName holds the Context Group Reference or another parameter for Concept Name of CODE passed from the template caller; CVCodeValue, CVCSD, and CVCodeMeaning hold the EV or DT value of CODE passed from the template caller; ConceptCode holds the Context Group Reference or another parameter of CODE content.

Figure 10:
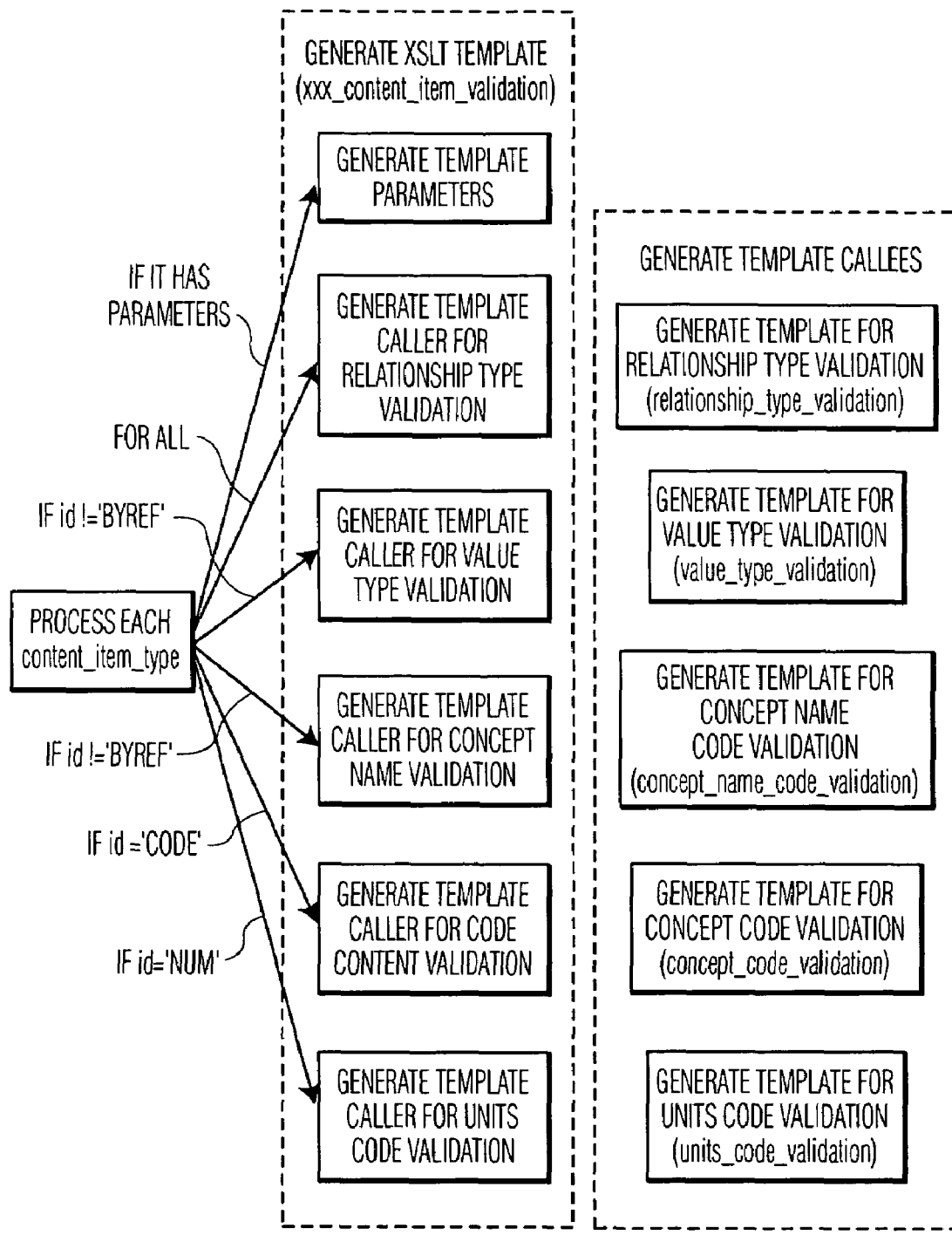
FIG. 10 illustrates the process of generating template for Content Item validation.

The process of generating XSLT templates for Content Item validation is shown in FIG. 10. For each content_item_type element, a template named xxx_content_item_validation is created (xxx is replace with its id value, for example CODE_content_item_validation). Such a template declares a template parameter for each parameter element and invokes the necessary templates.

A stylesheet for generating XSLT templates for validating Content Items of SR documents is implemented based on the flowchart of FIG. 10. By applying the same approach as shown in FIG. 4 using the XML instance mentioned early in this as input and the stylesheet mentioned above, the stylesheet for validating Content Items of SR documents is generated.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

The invention claimed is:

1. A method for validating a DICOM (Digital Imaging and Communications in Medicine) SR (Structured Reporting) XML (Extensible Markup Language) document using a processor, wherein the processor is arranged to perform the method, the method comprising acts of: (a) selecting an XML schema of DICOM SR IOD (Information Object Definitions); (b) selecting an XML parser to perform syntactic validation by checking structures, DICOM tag information, and data types of the DICOM SR document; (c) determining which DICOM SR template is used; (d) selecting an XSLT (Extensible Stylesheet Language Transformations) processor to perform semantic validation by validating a relationship type, value type, and coded concepts of a particular type of content item in the DICOM SR document against given values in the determined DICOM SR template; (e) generating validation result in XML; and (f) reporting the validation result.

2. A method of generating XSLT (Extensible Stylesheet Language Transformations) stylesheets from XML (Extensible Markup Language) representation of DICOM (Digital Imaging and Communications in Medicine) SR (Structured Reporting) templates using a processor, wherein the processor is arranged to perform the method, the method comprising acts of: (a) selecting an XML representation of a DICOM SR template; (b) selecting an XSLT stylesheet for generating XSLT stylesheets from an XML representation of DICOM SR templates; (c) selecting an XSLT processor to perform semantic validation by validating a relationship type, value type, and coded concepts of a particular type of content item in the DICOM SR document against given values in a determined DICOM SR template; (d) generating an XSLT stylesheet validating DICOM SR template constraints; and (e) reporting a validation result.

3. A framework method of developing XSLT (Extensible Stylesheet Language Transformations) stylesheets for generating XSLT stylesheets from an XML (Extensible Markup Language) representation of DICOM (Digital Imaging and Communications in Medicine) SR (Structured Reporting) templates using a processor, wherein the processor is arranged to perform the method, the method comprising acts of: (a) determining whether each of the DICOM SR templates is a root template or not; (b) if root template, first generating stylesheet inclusions for all invoked XSLT templates of sub DICOM SR templates; then generating a named XSLT template; (c) if not root template, generating a named XSLT template with XSLT template parameters for sub DICOM SR template parameters; (d) generating an anonymous XSLT template for DICOM SR template rows in the top or same level which performs passing template parameters if existing, checking the requirements of these rows, and validating the content against content constraints by calling the XSLT template for a single content item or a sub SR template using a template caller; (e) if a DICOM SR template row has nested template row(s), repeat step (d); (f) generating template callers based on the type of a DICOM SR template row; (g) if a single content item, the caller invokes an XSLT template for content item validation; (h) if a sub DICOM SR template, the caller invokes an XSLT template for DICOM SR sub template validation with parameters; and (i) if a composite content item having nested content items, the caller invokes an XSLT template for the current level content item and also invokes XSLT template for nested SR content item validation.

4. A method of developing XSLT (Extensible Stylesheet Language Transformations) stylesheets for generating XSLT stylesheets for validating content items, using a processor, wherein the processor is arranged to perform the method, the method comprising acts of: (a) creating an XML (Extensible Markup Language) document which includes a set of parameters used for content item validation; the numbers and names of these parameters are determined based on what type of content item; and (b) developing an XSLT stylesheet to transform the XML document from step -(a)-to an XSLT stylesheet by: determining whether a DICOM SR template is a root template or not; (c) if root template, first generating stylesheet inclusions for all invoked XSLT templates of sub DICOM SR templates; then generating a named XSLT template; (d) if not root template, generating a named XSLT template with XSLT template parameters for sub DICOM SR template parameters; (e) generating an anonymous XSLT template for DICOM SR template rows in the top or same level which performs passing template parameters if existing, checking the requirements of these rows, and validating the content against content constraints by calling the XSLT template for a single content item or a sub SR template using a template caller; (f) if a DICOM SR template row has nested template row(s), repeat step (e); (g) generating template callers based on the type of a DICOM SR template row; (h) if a single content item, the caller invokes an XSLT template for content item validation; (i) if a sub DICOM SR template, the caller invokes an XSLT template for DICOM SR sub template validation with parameters; and (j) if a composite content item having nested content items, the caller invokes an XSLT template for the current level content item and also invokes an XSLT template for nested SR content item validation.

* * * * *